(12) United States Patent  
Oonuma et al.

(10) Patent No.: US 9,194,878 B2  
(45) Date of Patent: Nov. 24, 2015

(54) AUTOMATIC ANALYSIS DEVICE

(75) Inventors: Mitsuru Oonuma, Tokyo (JP); Yoko Sato, Tokyo (JP); Hajime Yamazaki, Tokyo (JP); Akihito Wakui, Tokyo (JP)

(73) Assignee: Hitachi High-Technologies Corporation, Tokyo (JP)

( * ) Notice: Subject to any disclaimer, the term of this patent is extended or adjusted under 35 U.S.C. 154(b) by 0 days.

(21) Appl. No.: 14/347,450

(22) PCT Filed: Jul. 31, 2012

(86) PCT No.: PCT/JP2012/069471  
§ 371 (c)(1),  
(2), (4) Date: Mar. 26, 2014

(87) PCT Pub. No.: WO2013/046913  
PCT Pub. Date: Apr. 4, 2013

(65) Prior Publication Data  
US 2014/0241945 A1 Aug. 28, 2014

(30) Foreign Application Priority Data  
Sep. 28, 2011 (JP) ................................. 2011-213151

(51) Int. Cl.  
*G01N 35/10* (2006.01)  
*G01N 35/02* (2006.01)  
(Continued)

(52) U.S. Cl.  
CPC ............ *G01N 35/1002* (2013.01); *G01N 21/51* (2013.01); *G01N 35/025* (2013.01); *G01N 2035/00306* (2013.01); *G01N 2035/00316* (2013.01); *G01N 2035/0441* (2013.01)

(58) Field of Classification Search  
CPC .......... G01N 2035/00277; G01N 2035/00287; G01N 2035/00306; G01N 2035/00316; G01N 35/1002; G01N 35/025  
See application file for complete search history.

(56) References Cited

U.S. PATENT DOCUMENTS 4,517,160 A * 5/1985 Galle et al. ...................... 422/65  
5,855,847 A   1/1999 Oonuma et al.  
(Continued)

FOREIGN PATENT DOCUMENTS

EP    0733905 A2   9/1996  
EP    2317304 A1   5/2011  
(Continued)

OTHER PUBLICATIONS

Extended European Search Report received in corresponding European Application No. 12834704.4 dated Apr. 22, 2015.

*Primary Examiner* — Brian R Gordon  
(74) *Attorney, Agent, or Firm* — Mattingly & Malur, PC

(57) ABSTRACT

An automatic analysis device has a light scattering photometer incorporated therein, and improved accuracy resulting from reducing the influences from external light. The automatic analysis device includes a scattered light measurement unit disposed inside the main-body casing, and openable/closable protective covers to cover the top face of the main-body casing. A first protective cover at the center includes a light-shielding part to block external light. The protective covers include see-through parts enabling viewing of the inside. The light-shielding part is configured to cover an area of the reaction disk at least corresponding to the area above the scattered light measurement unit, thus reducing external light leaking into the scattered light measurement unit, and thus removing influences from external light on the scattered light measurement. The protective cover may have a divided structure.

11 Claims, 12 Drawing Sheets

(51) Int. Cl.
*G01N 21/51* (2006.01)
*G01N 35/04* (2006.01)
*G01N 35/00* (2006.01)

(56) References Cited

U.S. PATENT DOCUMENTS

| | | | |
|---|---|---|---|
| 6,042,786 A | 3/2000 | Oonuma et al. | |
| 2002/0025275 A1* | 2/2002 | Oonuma et al. | 422/64 |
| 2010/0284777 A1* | 11/2010 | Xiao et al. | 414/800 |
| 2012/0282683 A1 | 11/2012 | Mototsu | |

FOREIGN PATENT DOCUMENTS

| | | |
|---|---|---|
| JP | 63-132169 A | 6/1988 |
| JP | 08-094623 A | 4/1996 |
| JP | 10-048195 A | 2/1998 |
| JP | 2003-262642 A | 9/2003 |
| JP | 2004-101290 A | 4/2004 |
| JP | 2004101295 A | 4/2004 |
| JP | 2005-181007 A | 7/2005 |
| JP | 3141576 U | 5/2008 |
| JP | 2010-256345 A | 11/2010 |
| WO | 2011089966 A1 | 7/2011 |

* cited by examiner

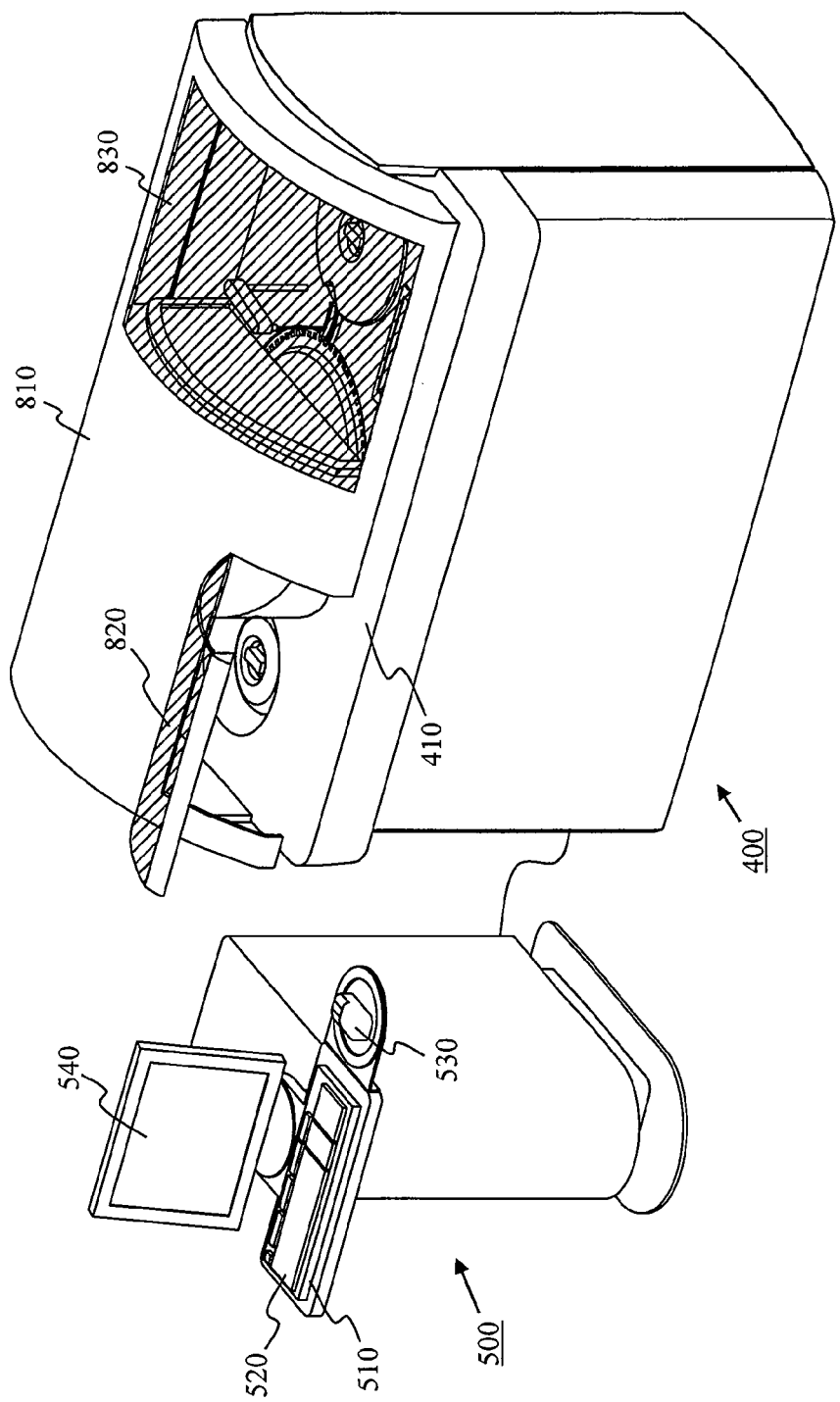

AUTOMATIC ANALYSIS DEVICE

TECHNICAL FIELD

The present invention relates to automatic analysis devices to analyze a biological sample such as blood and urine.

BACKGROUND ART

Clinical examination procedure for medical diagnosis includes a biochemical analysis and an immunological analysis for protein, sugar, lipid, enzymes, hormones, inorganic ions, disease markers in a biological sample such as blood and urine. Such clinical examination requires processing of a plurality of items to be examined reliably and quickly, and so a large part of the examination is executed by an automatic analysis device.

Reactions to be measured by an automatic analysis device mainly include two types of reactions that are color reactions between a substrate and an enzyme and immune reactions between an antigen and an antibody. An analysis based on the former reaction is called a biochemical analysis, and examines items such as LDH, ALP and AST. The biochemical analysis is to analyze, as an analysis target, a reaction liquid that is prepared by mixing a desired reagent with a sample such as serum, and to measure its absorbance. An analysis based on the latter reaction is called an immunity analysis, and examines items such as CRP, IgG and RF. Some substances to be measured in the latter case have an item to be examined, which requires quantification at a low-concentration area of a low blood level, and such an item is examined by a latex immunity analysis using, as a sensitizer, latex particles having a surface sensitized (bound) to an antibody.

Patent Literature 1 describes an automatic analysis device to measure the turbidity or the like of a liquid sample based on a change in diffused light, and the automatic analysis device described includes a light-shielding rotary cover with a dispensing hole so as to cover a reaction-container holding disk. After dispensing a reagent into a reaction container through the dispensing hole at the light-shielding rotary cover, and then rotating the light-shielding rotary cover until the dispensing hole is rotated from the above a photometer to the opposite side, measurement is performed while keeping the photometer in a dark-room state.

CITATION LIST

Patent Literature

Patent Literature 1: JP Patent Publication (Kokai) No. S63-132169

SUMMARY OF INVENTION

Technical Problem

In the latex immunity analysis, antibodies at the surface of latex particles included in a reagent recognizes antigens as a substance to be measured included in a sample and binds to them, and as a result, the latex particles agglutinate via the antigens, thus forming an agglutination of the latex particles. A conventional automatic analysis device is configured to irradiate a reaction liquid including this agglutination dispersed therein with light, and to measure the amount of light passing through the agglutination of the latex particles without being scattered. Higher concentration of the antigens makes the size of the agglutination larger after a certain period of time, and so more light is scattered thereby, meaning that the amount of light passing through decreases. Thus, the concentration of the antigens can be quantified based on the amount of light measured as reaction process data.

In recent years, the latex immunity analysis is required to have higher sensitivity. For higher sensitivity of the latex immunity analysis, a possible method considered is to measure a latex agglutination reaction with scattered light instead of transmitted light. In the case of measuring with scattered light, the strength of scattered light scattered by the agglutination of latex particles is very low, and it is susceptible to external light. Therefore, there is a need to avoid light external to the automatic analysis device from entering the light scattering photometer. There is another demand for an automatic analysis device, which is equipped with function units such as a sample dispensing function and a reagent dispensing function, to let an operator visually check whether the function units correctly function or not during the operation.

The technique described in Patent Literature 1 requires an additional driving system to rotary-drive the light-shielding rotary cover. The technique may lead to the possibility of contamination of the equipment due to dust or the like or of unexpected injury of the operator when the operator carelessly touches the equipment because the top face of the equipment is kept open during the analysis.

It is an object of the present invention to provide an automatic analysis device including a light scattering photometer incorporated therein, the automatic analysis device having improved analysis accuracy by reducing the influences from external light and that can be used safely with good operability.

Solution to Problem

An automatic analysis device of the present invention includes: a sample disk, a reagent disk, a reaction disk and a plurality of dispensing mechanisms that are disposed on a top face of a main-body casing, the sample disk holding a plurality samples, the reagent disk holding a plurality of types of reagent, the reaction disk holding a plurality of reaction cells, the plurality of dispensing mechanisms each including a nozzle fixed to the rotating arm and dispensing the samples and the reagent to the reaction cells held at the reaction disk. A scattered light measurement unit is disposed inside the main-body casing, and includes a light source that applies light to the reaction cells and a photoreceptor that receives scattered light generated from a reaction liquid in the reaction cells irradiated with the light. The automatic analysis device further includes a protective cover to cover the top face of the main-body casing openably/closably. The protective cover includes a light-shielding part to block external light and a see-through part enabling see therethrough of inside. The light-shielding part covers at least an area of the reaction disk corresponding to an area above the scattered light measurement unit.

Advantageous Effects of Invention

The present invention can provide an automatic analysis device that enables a high-precision analysis by reducing influences from external light, and that can be used safely with good operability.

Problems, configurations, and effects other than those explained above will be made apparent by the following explanation of embodiments.

BRIEF DESCRIPTION OF DRAWINGS

FIG. 13 schematically shows still another embodiment of the automatic analysis device according to the present invention.

DESCRIPTION OF EMBODIMENTS

The following describes embodiments of the present invention, with reference to the drawings.

Figure 1:
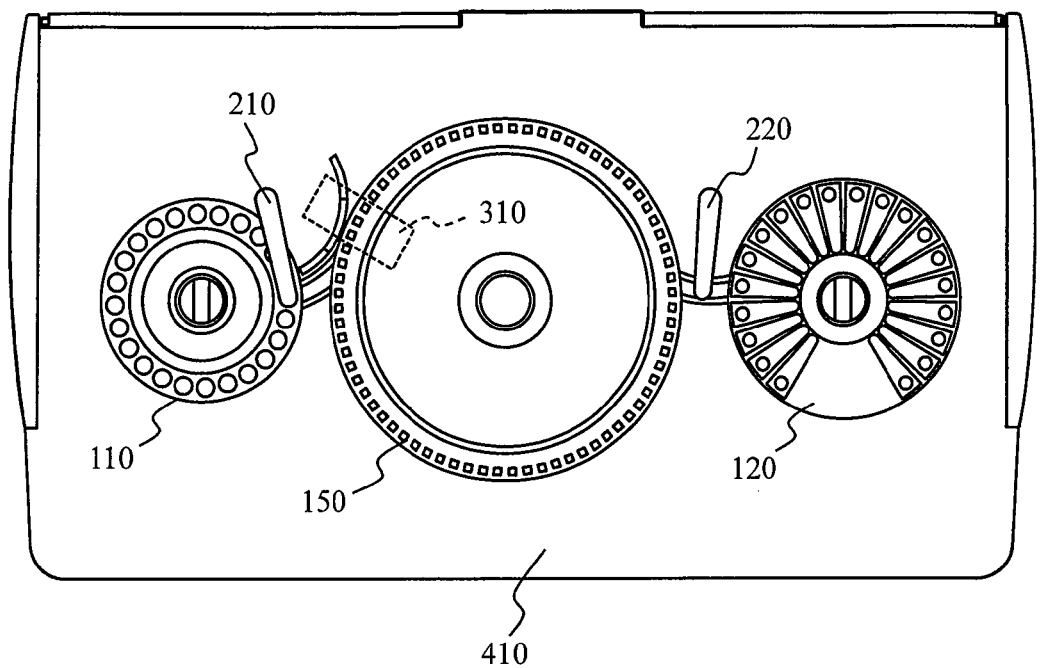
FIG. 1 schematically shows the layout of elements at a top face of a main-body casing of an exemplary automatic analysis device according to the present invention.

FIG. 1 schematically shows the layout of elements at a top face 410 of a main-body casing of an exemplary automatic analysis device according to the present invention. The automatic analysis device of the present embodiment includes a sample disk 110, a reagent disk 120, a reaction disk 150, a sample dispensing mechanism 210, and a reagent dispensing mechanism 220 disposed at the top face of the main-body casing. In the present embodiment, the reaction disk 150 is disposed at a center in the horizontal direction of the drawing at the top face 410 of the main-body casing, and the reagent disk 120 and the reagent dispensing mechanism 220 are disposed on the right side of the reaction disk. The sample disk 110 and the sample dispensing mechanism 210 are disposed on the left side of the reaction disk 150. The reagent disk is equipped with a cooling function to store reagents, and the upper part thereof is covered with a reagent disk lid. Although one reagent disk is provided in this example, a plurality of disks may be, of course, disposed, and the reagent dispensing mechanism can be increased in number depending on the number or the layout of the reagent disks.

The automatic analysis device includes a stirrer unit to stir a mixture liquid in a reaction cell, a reaction cell washing unit to wash reaction cells, a nozzle washing unit to wash a nozzle of a dispensing function and the like. The main-body casing internally includes various types of equipment to make up the analysis device, which is not illustrated, as well as a power supply to drive such equipment, a control mechanism, a constant temperature bath, a washing pump and the like. They are not important for the elements of the present invention and are provided in a conventional automatic analysis device as well, and so their illustration and detailed descriptions are omitted.

The automatic analysis device of the present invention can execute scattered light measurement concurrently with absorbance measurement. The main-body casing internally includes a scattered light measurement unit 310 to measure scattered light from a reaction liquid at a designated area on the circumference of the reaction disk 150. The scattered light measurement unit 310 of the present embodiment is disposed on the left side of the center of the reaction disk 150 in FIG. 1. The scattered light measurement unit 310 is disposed at an area overlapping with a travelling path of the sample dispensing mechanism 210.

Figure 2:
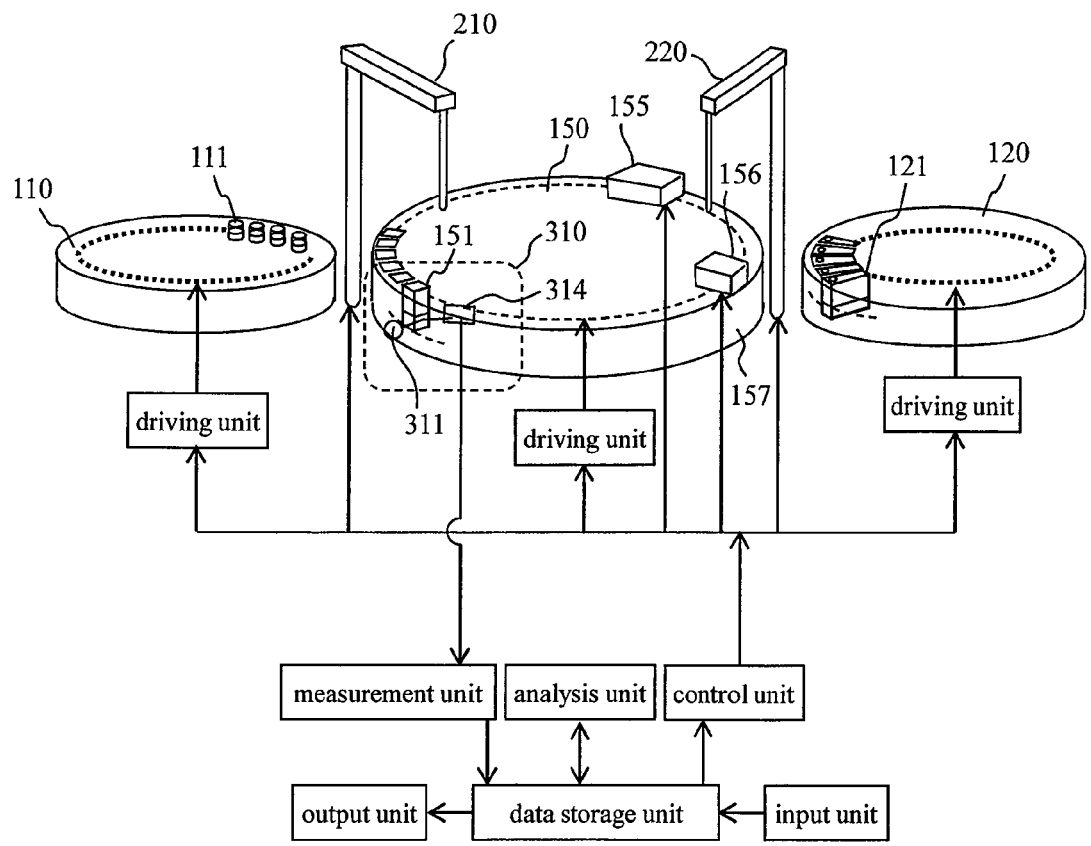
FIG. 2 schematically shows an exemplary overall configuration of an automatic analysis device.

FIG. 2 schematically shows an exemplary overall configuration of the automatic analysis device of FIG. 1 including a control system.

On the sample disk 110, a plurality of sample cups 111 containing samples is disposed. On the reagent disk 120, a plurality of reagent bottles 121 containing reagents is disposed. On the circumference of the reaction disk 150, a plurality of reaction cells 151 is disposed, so as to allow a sample and a reagent to be mixed therein to prepare a reaction liquid. The sample dispensing mechanism 210 includes an arm that rotates around a support column as an axis and a nozzle fixed to the arm, and is to dispense a fixed amount of sample into a reaction cell 151 from a sample cup 111. The reagent dispensing mechanism 220 includes an arm that rotates around a support column as an axis and a nozzle fixed to the arm, and is to dispense a fixed amount of reagent into a reaction cell 151 from a reagent bottle 121. A stirrer unit 155 is to stir a sample and a reagent in a reaction cell 151 for mixture. A reaction cell washing unit 156 is to let a reaction liquid out from the reaction cell 151 and wash the reaction cell after the analysis of the reaction liquid is finished. Then a next sample is dispensed again to the washed reaction cell 151 from the sample dispensing mechanism 210, and a new reagent is dispensed from the reagent dispensing mechanism 220, and the reaction cell is used for another reaction. The reaction cells 151 are immersed in a constant-temperature fluid 157 in the constant temperature bath whose temperature and flow rate are controlled, so as to move the reaction cells 151 and the reaction liquid contained therein while keeping the temperatures of them at a constant temperature. Exemplary constant-temperature fluid 157 used includes water, and the temperature of the constant-temperature fluid is adjusted to be 37±0.1° C. by a control unit. At a part of the circumference of the reaction disk 150, the scattered light measurement unit 310 is provided.

Figure 3:
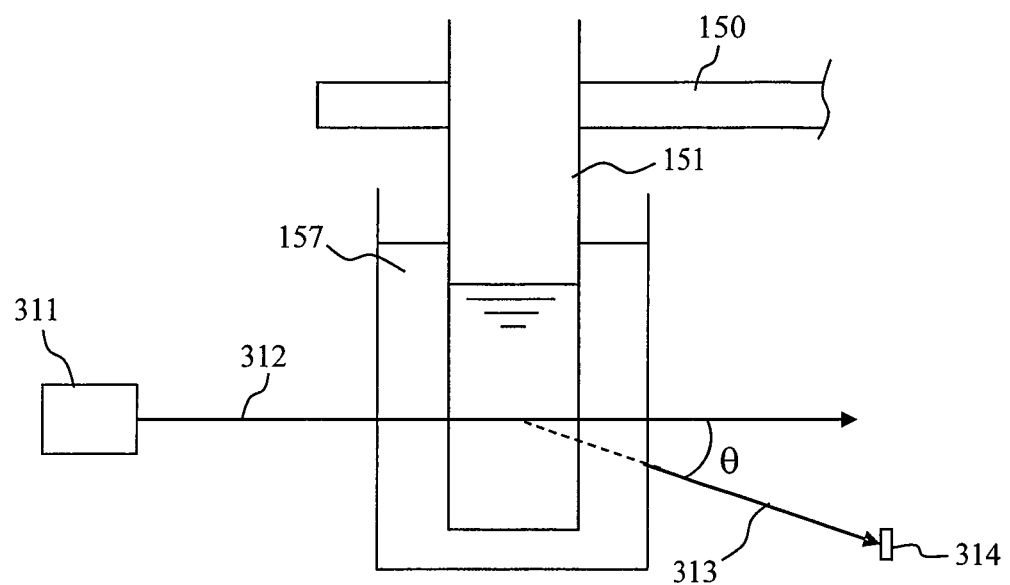
FIG. 3 schematically shows the scattered light measurement unit.

FIG. 3 schematically shows the scattered light measurement unit. The scattered light measurement unit is internally provided in the main-body casing, and includes a light source to apply light to a reaction cell, and a photoreceptor to receive scattered light generated from a reaction liquid irradiated with light in the reaction cell. Exemplary light source 311 used includes a LED light source, and irradiation light 312 from the light source 311 is applied to a moving reaction cell 151, and scattered light 313 is received at a scattered light photoreceptor 314. The irradiation light from the light source 311 may have a wavelength of 700 nm, for example. The scattered light photoreceptor 314 measures scattered light 313 that is scattered in the direction away from the optical axis by angle θ. The angle θ may be θ=20°, for example. Data on the amount of scattered light received by the scattered light photoreceptor 314 is sent to a data storage unit in a PC via a measurement unit.

The procedure to quantify the concentration of a substance to be measured in a sample is as follows. Firstly, a fixed amount of sample in a sample cup 111 is dispensed into a reaction cell 151 by the sample dispensing mechanism 210.

Next, a fixed amount of reagent in a reagent bottle 121 is dispensed into the reaction cell 151 by the reagent dispensing mechanism 220. For dispensing of them, the sample disk 110, the reagent disk 120 and the reaction disk 150 are rotary driven by their respective driving units under the control of the control unit, and the sample cups 111, the reagent bottles 121 and the reaction cells 151 are moved in time with the dispensing timing of the dispensing mechanisms 210, 220. Subsequently, the dispensed sample and reagent in the reaction cell 151 are stirred by the stirrer unit 155 to be a reaction liquid. Scattered light from the reaction liquid is measured during the rotation of the reaction disk 150 every time the scattered light passes through the scattered light measurement unit 310, and the measurements from the measurement unit are stored one by one as reaction process data in a data storage unit. After measurement for a certain period of time, e.g., for about 10 minutes, the inside of the reaction cell 151 is washed by the reaction cell washing unit 156, and the procedure goes to an analysis for a next examination item. In this way, reaction process data of the reaction liquid at regular time intervals is stored in the data storage unit. Based on the stored reaction process data from the scattered light measurement unit, an analysis unit finds a change in light amount due to a reaction for the certain time period, and calculates a quantification result based on calibration curve data held in the data storage unit beforehand, which is displayed by an output unit. Data necessary to control and analysis of the units is input from an input unit to the data storage unit. Various types of data and analysis results stored in the data storage unit as well as an alarm are output from the output unit by displaying, for example.

The automatic analysis device of the present invention includes a scattered light measurement unit to detect scattered light scattered from a reaction liquid for improved analysis accuracy. Scattered light detected by the scattered light measurement unit, however, is very weak, and influences thereon from external light cannot be ignored, and so there is a need to block light so as not to let external light incident on the scattered light measurement unit. Herein, external light mainly enters the scattered light photoreceptor of the scattered light measurement unit via an upper opening part of each reaction cell. If external light enters a reaction cell from its upper opening part that is open to enable dispensing of a sample or a reagent, then a part of it is scattered by a wall part of the reaction cell or a surrounding structure, and is detected by the scattered light photoreceptor, which causes noise. Since the reaction disk includes a plurality of reaction cells disposed thereon at narrow intervals in an adjacent manner, disturbance light may be incident on the scattered light photoreceptor of the scattered light measurement unit via a reaction cell adjacent to the reaction cell performing scattered light measurement. Therefore, in order to prevent external light from entering the scattered light photoreceptor, it is effective to block light over the possible wide range of the reaction disk at least at an area overlapping with the area above the scattered light measurement unit.

Meanwhile, the sample disk is frequently accessed to mount a set of new sample cups or to load a sample cup containing a sample that has to be analyzed by interruption. That is, an automatic analysis device has to be configured to enable access to a sample disk while keeping the light-shielding state of external light at the scattered light measurement unit. An automatic analysis device is preferably configured to enable visual checking of the motion of a dispensing mechanism or the like during the operation.

The present invention meets such a request by devising the structure of an openable/closable protective cover that covers the upper part of the main-body casing of the automatic analysis device. The protective cover has a light-shielding part to block external light and a see-through part to see the inside therethrough. The light-shielding part is to cover at least an area of the reaction disk corresponding to the area above the scattered light measurement unit, thus reducing external light leaking to the scattered light measurement unit, and thus removing influences from external light on the scattered light measurement.

The openable/closable protective cover may have a two-divided structure or a three-divided structure. A two-divided structured protective cover includes a first protective cover defining a light-shielding part and a second protective cover including a see-through part. In this case, the second protective cover is openable/closable independently, and the first protective cover defining the light-shielding part is configured to be openable after the second protective cover is opened or to be not openable unless it is opened concurrently with the second protective cover.

The three-divided structured protective cover includes a first protective cover defining a light-shielding part, a second protective cover and a third protective cover that are located on either side of the first protective cover, each including a see-through part. In this case, the second protective cover and the third protective cover are openable/closable independently, and the first protective cover defining the light-shielding part is configured to be openable after the second protective cover and the third protective cover are opened or to be not openable unless it is opened concurrently with opening of the second protective cover and the third protective cover.

The following describes a specific structure of the automatic analysis device provided with an openable/closable protective cover.

Embodiment 1

Figure 4:
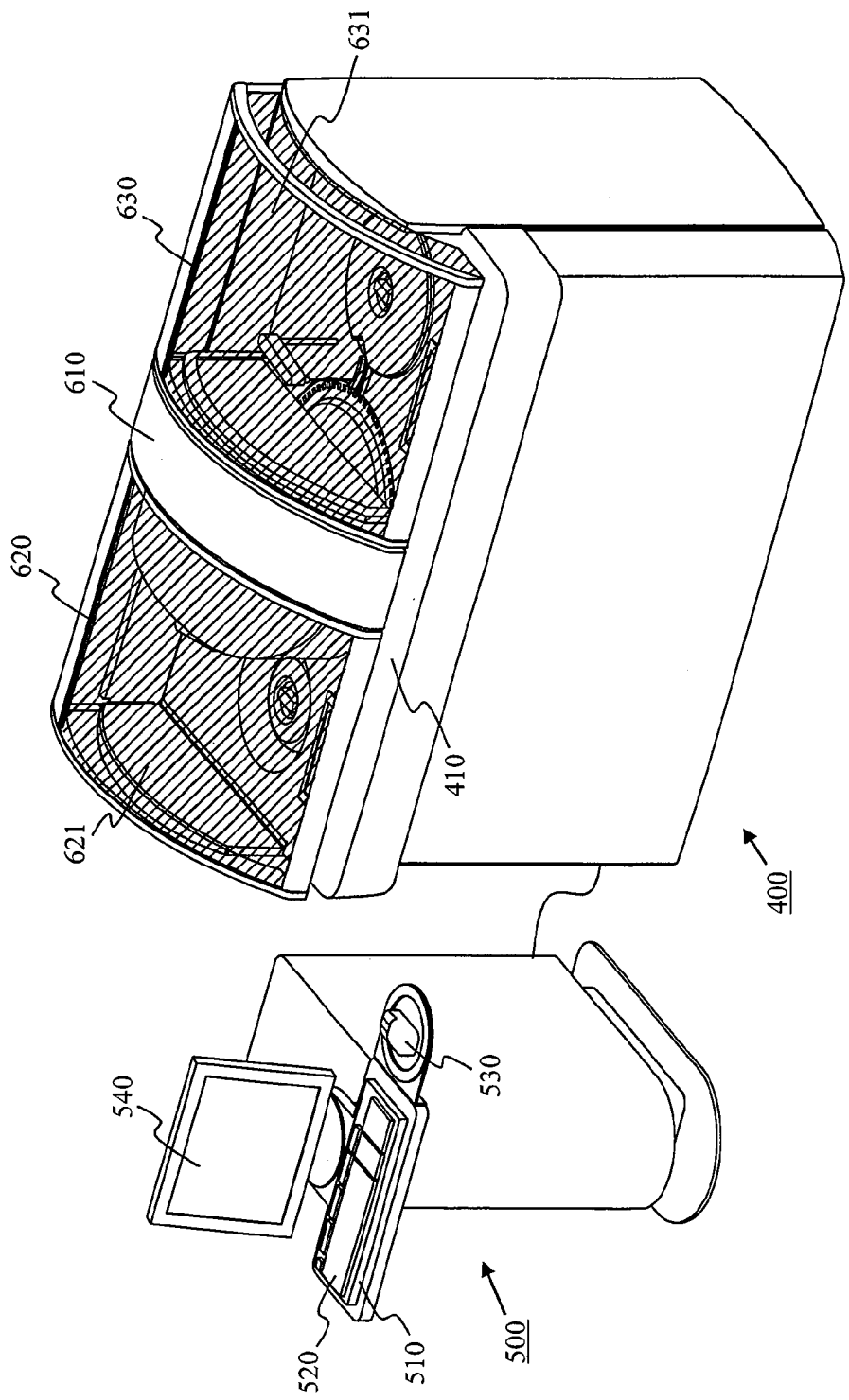
FIG. 4 is a perspective view schematically showing one embodiment of the automatic analysis device according to the present invention.

FIG. 4 is a perspective view schematically showing Embodiment 1 of the automatic analysis device according to the present invention. The automatic analysis device of the present embodiment includes an analysis device main body 400 and a manipulation/control unit 500. The top face of the casing of the main body of the analysis device of the present embodiment is covered with three protective covers 610, 620, 630. A first protective cover 610 located at the center is a protective cover to block light so as not to let external light in the scattered light measurement unit provided inside of the casing of the main body, and is made of an opaque material not to transmit light. The second protective cover 620 disposed on the left of the first protective cover 610 is a protective cover to cover the sample disk 110, and includes a see-through part 621 that is made of a light-transmissive material to enable observation of the inside. The third protective cover 630 disposed on the right of the first protective cover 610 is a cover to cover the reagent disk 120, and includes a see-through part 631 that is made of a light-transmissive material to enable observation of the inside. The see-through parts 621, 631 do not have to be necessarily made of a high light-transmissive material that is clear and colorless, and may be colored as long as it enables seeing therethrough. The second protective cover 620 and the third protective cover 630 as a whole may be made of a light-transmissive material. Operators are allowed to visually check the states of various disks and the motion of dispensing mechanisms through the see-through parts 621, 631 of the protective covers while keeping the protective covers closed, thus knowing the operation state of the device easily and so they can continue the analysis with security.

The manipulation/control unit 500 includes a PC 510, an input unit including a keyboard 520 and a mouse 530, and an output unit including a display 540. The PC 510 has a memory to store software to implement the functions of the measurement unit, the analysis unit, the control unit and the data storage unit shown in FIG. 2.

Figure 5:
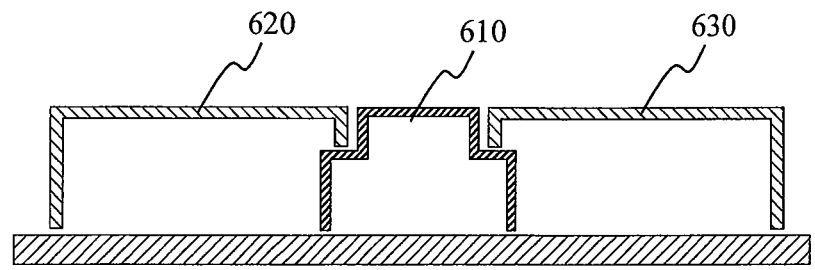
FIG. 5 is a cross-sectional view schematically showing the overlapping state of protective covers.

FIG. 5 is a cross-sectional view schematically showing the overlapping state of the three protective covers. The first protective cover 610 covering the area above the reaction disk and the scattered light measurement unit is a light-shielding cover, and for higher-degree of light-shielding, the first protective cover 610 at the center is located below the second protective cover 620 and the third protective cover 630 on either side. In other words, a part of the second protective cover 620 is overlapped on a part of the first protective cover 610 and a part of the third protective cover 630 is overlapped on a part of the first protective cover 610 when all of the covers are closed. With this configuration, each of the second protective cover 620 and the third protective cover 630 can be opened/closed alone freely. The first protective cover 610 at the center is configured so as to be openable after the protective covers on either side are opened or not to be openable unless it is opened concurrently with the protective covers on either side.

Among the reaction disk, the sample disk, and the reagent disk, the sample disk and the reagent disk have to be accessed by an operator during the operation of the automatic analysis device. If the first protective cover 610 at the center is opened during the operation, external light enters the scattered light photoreceptor of the scattered light measurement unit, and so measurement data that is measured on a time-series basis becomes useless. Therefore, the operator has to minimize the opening of the first protective cover 610 at the center during the operation of the automatic analysis device. Actually the first protective cover 610 at the center has to be opened only at the maintenance of the device. In this way, the sample disk and the reagent disk have to be accessed during the operation of the device, and a light-shielding state of the scattered light measurement unit from external light has to be kept, and so the configuration is significant, which allows the first protective cover 610 at the center, which is less frequently opened, to be opened after the protective covers 620, 630 on either side are opened, or allows it not to be opened unless it is opened concurrently with the opening of the protective covers 620, 630 on either side.

Figure 6:
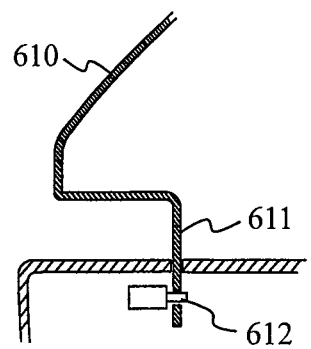
FIG. 6 is a cross-sectional view schematically showing an exemplary lock mechanism.

The first protective cover 610 at the center having a function to block light may be equipped with a lock mechanism so as to prevent the operator from opening the cover carelessly during the operation of the automatic analysis device. FIG. 6 is a cross-sectional view schematically showing an exemplary lock mechanism. The lock mechanism of the present embodiment includes a tongue part 611 extending downward at a part of the first protective cover 610 facing a face of the main-body casing, and the tongue part 611 has a hole bored therein, into which a pin 612 fixed to the main-body casing is inserted, so as to fix the first protective cover 610 to the main-body casing. The pin 612 may be configured to be automatically inserted into the hole of the tongue part 611 when the first protective cover is closed to push the tongue part 611 downward. Alternatively, upon receiving an instruction for locking of the first protective cover 610 from the manipulation/control unit 500, the pin 612 may be driven in the protruding direction. To unlock for maintenance of the device, for example, an instruction for unlocking may be issued from the manipulation/control unit 500. Then, the pin 612 moves backward and is detached from the tongue part 611, thus making the first protective cover 610 openable.

A sensor may be provided to detect the opening/closing state of the first protective cover 610, and if the first protective cover 610 is not closed, an alarm may be displayed on a display part 540 or the starting of the operation of the automatic analysis device may be disabled. Exemplary sensors to detect the opening/closing state of the first protective cover 610 include any sensor such as existing proximity sensor or contact sensor. Alternatively, the locking state of the first protective cover by the aforementioned lock mechanism is considered as closing of the protective cover and the unlocking state is considered as opening of the protective cover, so that such a lock mechanism can be used instead of the sensor to detect the opening/closing state of the first protective cover.

Figure 7:
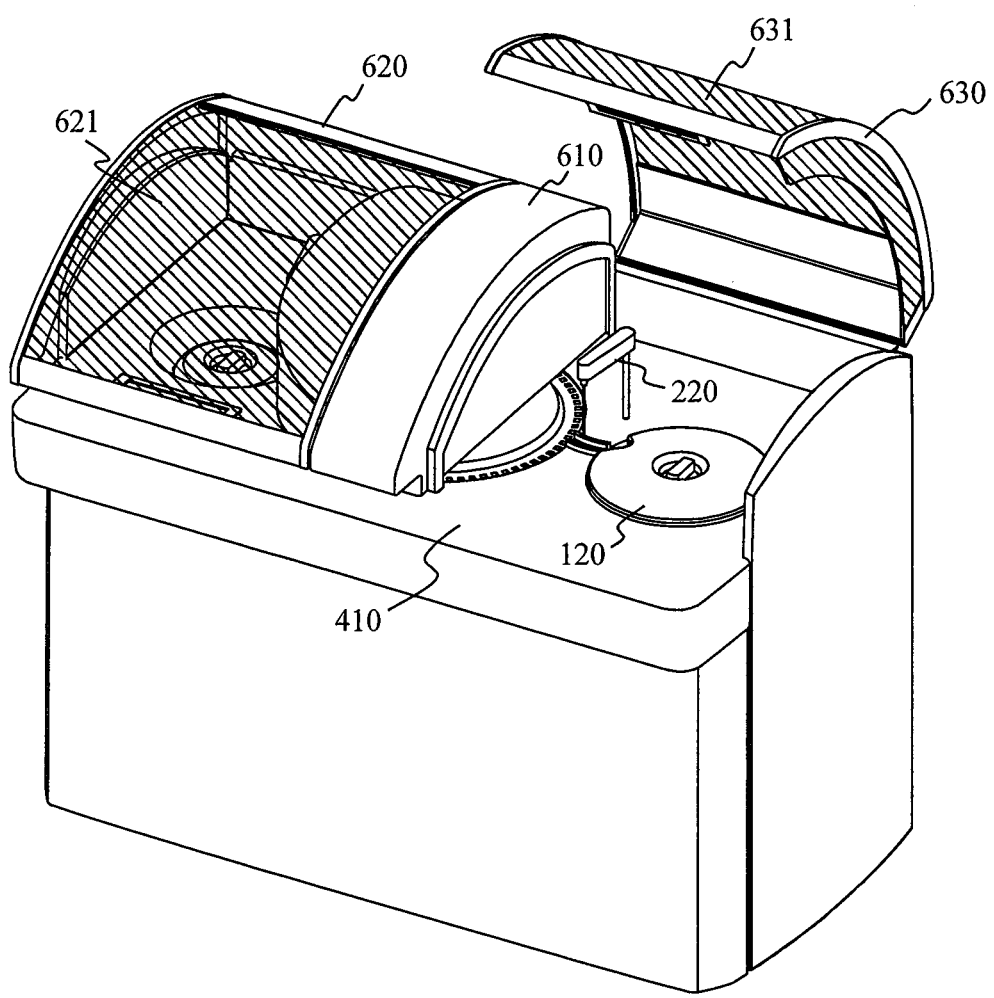
FIG. 7 shows a state where the right-side protective cover is open.

FIG. 7 shows a state where the third protective cover 630 to cover the reagent disk 120 is opened. In this state, the reagent disk lid covering the area above the reagent disk 120 is removed, and so a reagent can be added or refilled. Such a second protective cover 620 or third protective cover 630 that are opened/closed frequently can be opened while closing the first protective cover 610 at the center, and so the light-shielding state of the scattered light measurement unit from external light can be kept. As a result, interruption of a sample or addition or refilling of a reagent can be performed anytime without stopping measurement during the operation of the automatic analysis device.

Figure 8:
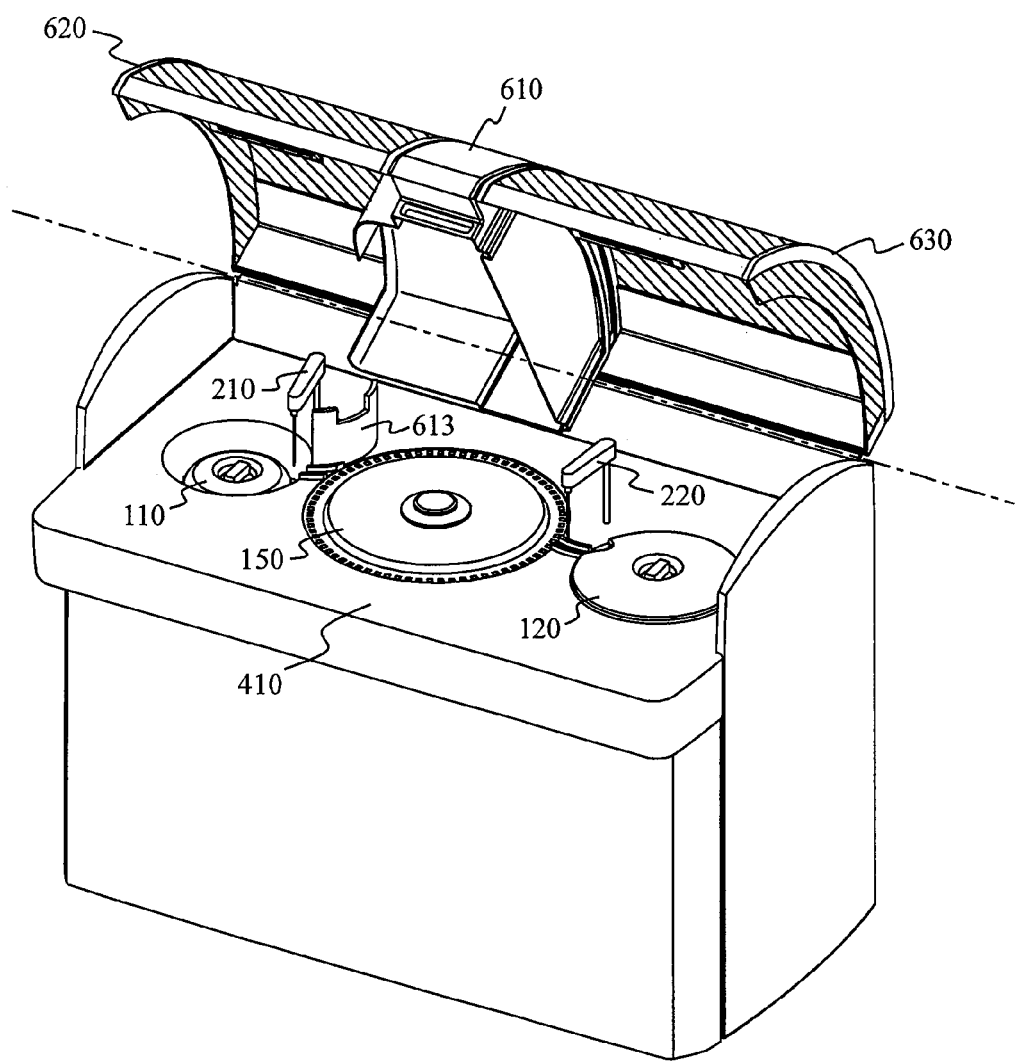
FIG. 8 shows a state where all of the protective covers are open.

FIG. 8 shows a state where the first, the second and the third protective covers 610, 620, 630 are all open. The first, the second and the third protective covers have rotary axes at their rear end parts, which are configured coaxially as shown with a dot-and-dash line in the drawing. Therefore, the three protective covers can be opened/closed concurrently and smoothly. In this way, when the three protective covers are all open, fully-access is enabled to the top face 410 of the main-body casing, whereby an operator can freely perform the maintenance operations such as cleaning of the top face 410 of the main-body casing, checking the states of the sample dispensing mechanism 210 and the reagent dispensing mechanism 220 and cleaning of them, washing and replacing of reaction containers without constraints. As shown in the drawing, the top face 410 of the main-body casing is provided with a light-shielding wall 613 near the reaction disk 150, the light-shielding wall 613 partially playing a role of the light-shielding function in corporation with the first protective cover 610. Details of this light-shielding wall 613 are described later. The first protective cover 610 in corporation with the light-shielding wall 613 defines, at an area above the scattered light measurement unit, a quasi-closed space to minimize entering of external light therein from the above or the side, thus preventing external light from being incident on the scattered light photoreceptor of the scattered light measurement unit through reaction cells disposed on the reaction disk 150 or the like.

Figure 9:
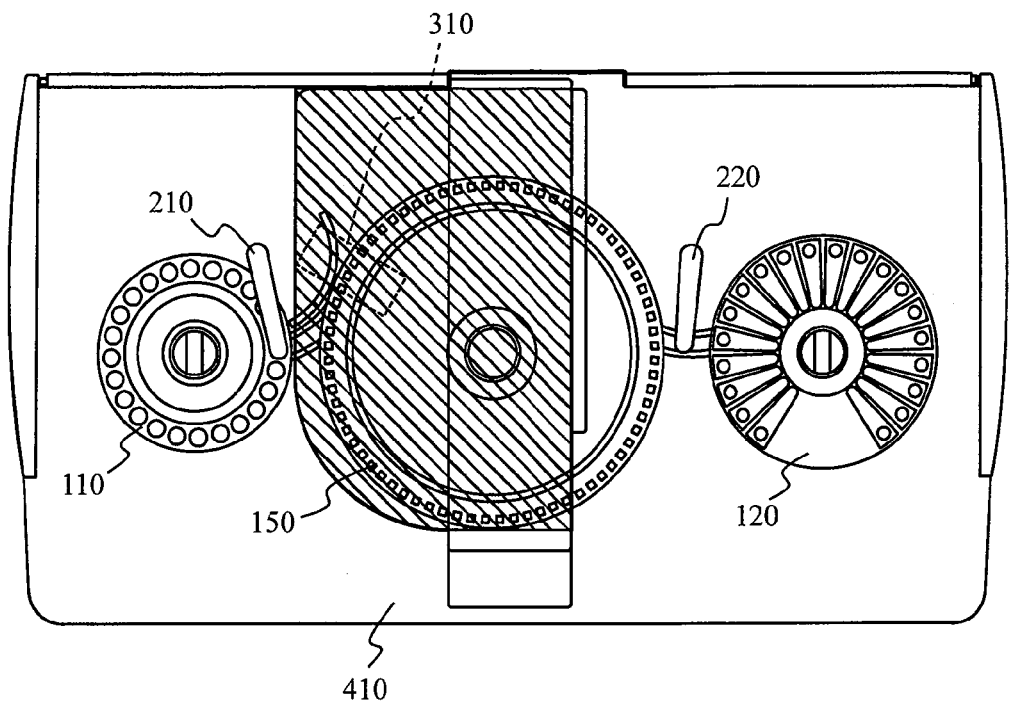
FIG. 9 shows the light-shielding range by a protective cover.

FIG. 9 shows the light-shielding range by the first protective cover 610. The scattered light measurement unit 310 of the present embodiment is disposed at the illustrated area inside of the main-body casing. Especially the scattered light measurement unit 310 has to be shielded from external light because scattered light generated from a reaction liquid is weak, and so if external light leaks into the scattered light photoreceptor, the measurement accuracy deteriorates. External light mainly enters the inside of the casing through upper opening parts of reaction cells disposed on the reaction disk 150, and leaks into the scattered light photoreceptor 314 of the scattered light measurement unit 310 disposed inside of the casing. External light leaking into through a reaction cell performing scattered light measurement influences the most on the scattered light measurement, and then external light entering through a neighboring reaction cell influences the second most, and it can be considered that external light passing through a reaction cell disposed away from the scattered light photoreceptor influences less.

Although it is perfect that light-shielding can cover the area above the reaction disk 150 as a whole, interference with mechanical systems such as the reagent dispensing mechanism 220 and the sample dispensing mechanism 210 and accessibility to the sample disk 110 and the reagent disk 120 also has to be considered. It is further requested to enable visual checking of the motion of the mechanical systems. To this end, the light-shielding range has to be a possible wide range capable of covering the area of the reaction disk 150 corresponding to at least the area above the scattered light measurement unit 310, and the present embodiment sets this range as that shown with hatching in the drawing. That is, the limit of the light-shielding range is set as follows. The light-shielding range is set on the right side of the reaction disk 150 where the reagent disk 120 is disposed, i.e., at the upper part of the casing on the opposite side of the scattered light measurement unit 310 provided with reference to the center of the reaction disk 150 so that the limit of the light shielding range does not overlap with the movable range of the reagent dispensing mechanism 220. Then, the light-shielding range is set on the left side of the reaction disk 150 where the sample disk 110 is disposed, i.e., at the upper part of the casing on the side of the scattered light measurement unit 310 provided with reference to the center of the reaction disk 150 so that a part above the sample disk 110 is opened so as not to interfere with an access to the sample disk 110.

Figure 10:
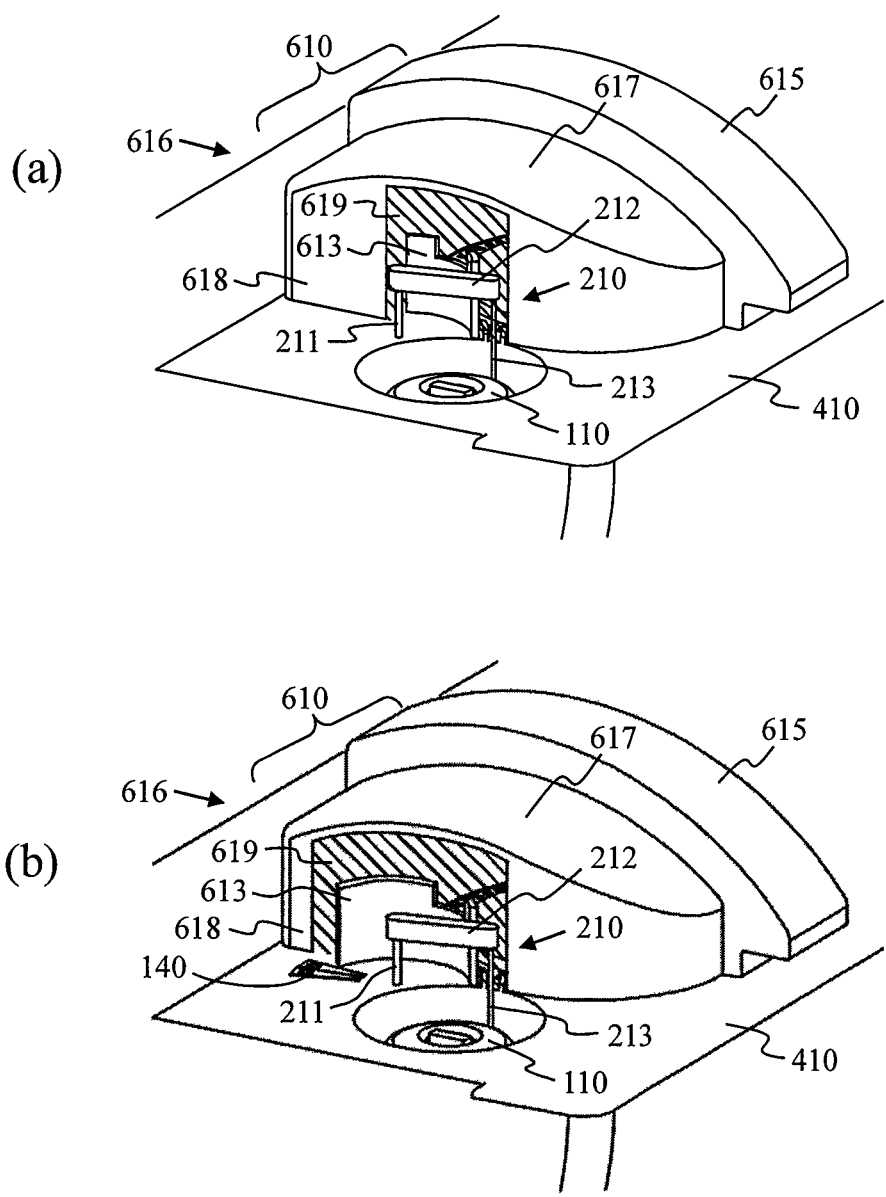
FIGS. 10(a) and 10(b) show a relationship between a protective cover and a light-shielding wall.

FIG. 10 shows a relationship between the first protective cover 610 and the light-shielding wall 613 in details. In FIG. 10(a), the sample dispensing mechanism 210 includes a support column 211 that is movable vertically, an arm 212 fixed to an upper part of the support column, and a nozzle 213 fixed to the forwarding end of the arm and extending downward. In this way, the nozzle 213 to suck or discharge a sample or a reagent has a tip end that rotates around the support column 211 as an axis and can move vertically. When a sample is dispensed to a reaction cell, the sample dispensing mechanism 210 rotary-moves around the support column 211 as an axis, and moves the tip end of the nozzle 213 between above the sample disk 110 and above the reaction disk 150. Alternatively as shown in FIG. 10(b), a reagent holding area 140 may be provided separately for a reaction cell to hold a reagent, and when the reagent is dispensed from this area 140, the sample dispensing mechanism 210 may rotary-move around the support column 211 as an axis, and moves the tip end of the nozzle 213 between above the reagent holding area 140 and above the reaction disk 150.

The first protective cover 610 includes a main-body part 615, and a protruding part 616 extending downward below the second protective cover 620 from the main-body part 615. The main-body part 615 has a constant width, and has a surface that is curved in the shape substantially same as that of the second protective cover 620 and the third protective cover 630 on either side, so that when the three protective covers are closed, one continuous curved surface is defined as shown in FIG. 4. The present embodiment illustrates curved protective covers, and they may have a structure whose shape changes in a step-wise manner or may have a linear shape.

The protruding part 616 includes a roof part 617 and a side wall 618, and the side wall 618 is provided with an opening 619. The roof part 617 of the protruding part 616 overhangs so as to cover an area above a part of the nozzle travelling path of the sample dispensing mechanism 210, thus shielding light entering the top face 410 of the main-body casing from the above so as not to enter the internal space defined by the first protective cover 610.

The arm 212 and the nozzle 213 of the sample dispensing mechanism 210 move between the sample disk 110 and the reaction disk 150 or in the example of FIG. 10(b), move between the reagent holding area 140 and the reaction disk 150. Then, the first protective cover 610 has the opening 619 at the side wall 618 at an area intersecting the nozzle travelling path of the sample dispensing mechanism 210 so as not to interfere with such a motion, and so light-shielding is not sufficient in this case. Then, the present embodiment provides the light-shielding wall 613 at a position slightly closer to the support column 211 from the arc-shaped nozzle travelling path of the sample dispensing mechanism 210, the light-shielding wall 613 having a shape not to interfere with the moving of the arm 212 and the nozzle 213 and being curved like an arc along the nozzle travelling path. This light-shielding wall 613 can cover the most part of the opening 619 provided at the side wall 618 of the protruding part 616, and so prevents external light from entering above the reaction disk 150 from the side below the roof part 617 of the first protective cover 610, thus enhancing the light-shielding performance. The light-shielding wall 613 is fixed to the top face 410 of the main-body casing. The opening 619 provided at the side wall 618 of the first protective cover 610 facing the sample dispensing mechanism 210 and the light-shielding wall 613 define a slit-like gap having a size allowing free motions of the arm 212 and the nozzle 213 of the sample dispensing mechanism 210. With this configuration, a demand for decrease in external light that leaks into the scattered light measurement unit 310 located below the reaction disk 150 can be met while enabling an access of the nozzle 213 of the sample dispensing mechanism 210 to above the reaction disk 150.

That is an example provided with the light-shielding wall 613 having a shape not to interfere with the moving of the arm 212 and the nozzle 213 and being curved like an arc along the nozzle travelling path at a position slightly closer to the support column 211 from the arc-shaped nozzle travelling path of the sample dispensing mechanism 210, and the light-shielding wall is not necessarily curved as long as it has a shape not to interfere with the moving of the nozzle. The above describes the arc-like travelling path of the nozzle 213, which is not a limiting example.

Figure 11:
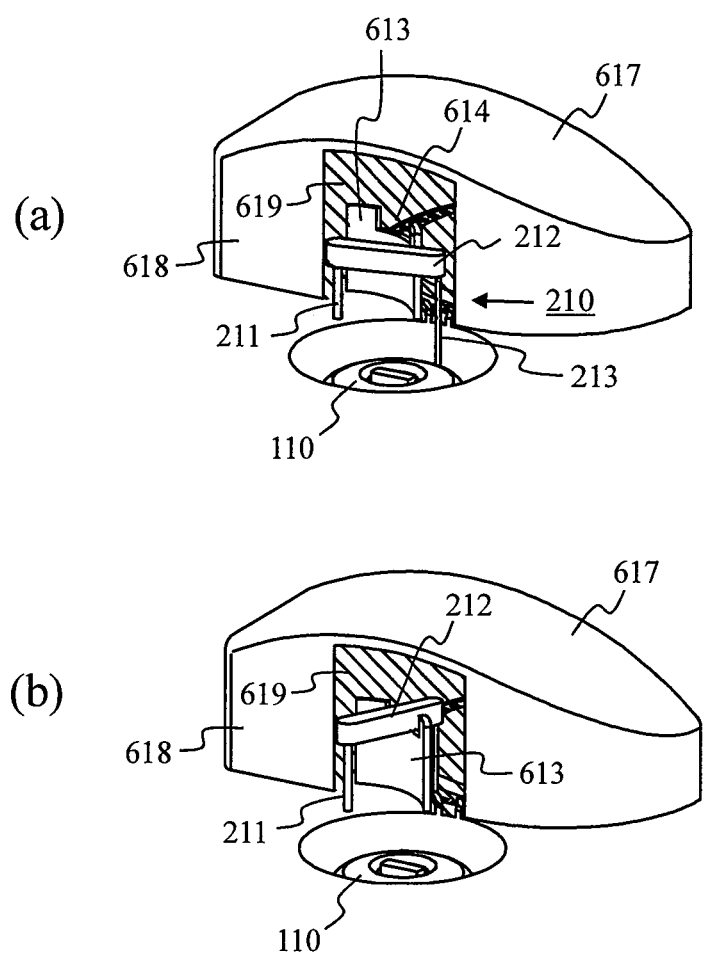
FIGS. 11(a) and 11(b) show a relationship between a light-shielding wall and a dispensing mechanism.

FIG. 11 explains a relationship between the light-shielding wall 613 and the sample dispensing mechanism 210. The light-shielding wall 613 has, at its upper part, a cutout 614 at a position corresponding to the arm position when the nozzle 213 is positioned at a reaction cell of the reaction disk.

FIG. 11(a) shows a state where the nozzle 213 of the sample dispensing mechanism 210 is located above the sample disk to suck a sample. In order to suck a sample in a sample cup held at the sample disk securely, the arm 212 is moved down so as to insert the nozzle 213 to a bottom part of the sample cup for suction. FIG. 11(b) shows a state where a sample sucked is discharged to a reaction cell held at the reaction disk. The arm 212 is rotated until the tip end of the nozzle is located above the reaction cell held at the reaction disk. At this time, the arm 212 of the sample dispensing mechanism is located above the cutout 614 provided at the light-shielding wall 613. At this position, the arm 212 and the nozzle of the sample dispensing mechanism are moved down. The cutout 614 of the light-shielding wall 613 is designed so as not to interfere with the moving-down of the arm 212 at this position by a predetermined amount. In this way, the sample dispensing mechanism 210 inserts the tip end of the nozzle into the reaction cell securely to let the sucked sample discharged into the reaction cell.

The arm 212 of the sample dispensing mechanism 210 passes through a gap in the horizontal direction defined between the opening 619 provided at the side wall 618 of the first protective cover 610 and an upper end part of the light-shielding wall 613, and the nozzle 213 passes through a gap in the vertical direction defined by the opening 619 provided at the side wall 618 and a side end part of the light-shielding wall 613, and so the motion of the sample dispensing mechanism 210 is not interfered. The slit-like gap defined by the opening 619 provided at the side wall of the first protective cover 610 and the light-shielding wall 613 is a narrow gap just letting the arm 212 and the nozzle 213 of the sample dispensing mechanism 210 pass therethrough. In this way, external light entering onto the reaction disk 150 from the side face of the first protective cover 610 on the side of the sample disk 110 can be minimized.

Embodiment 2

Figure 12:
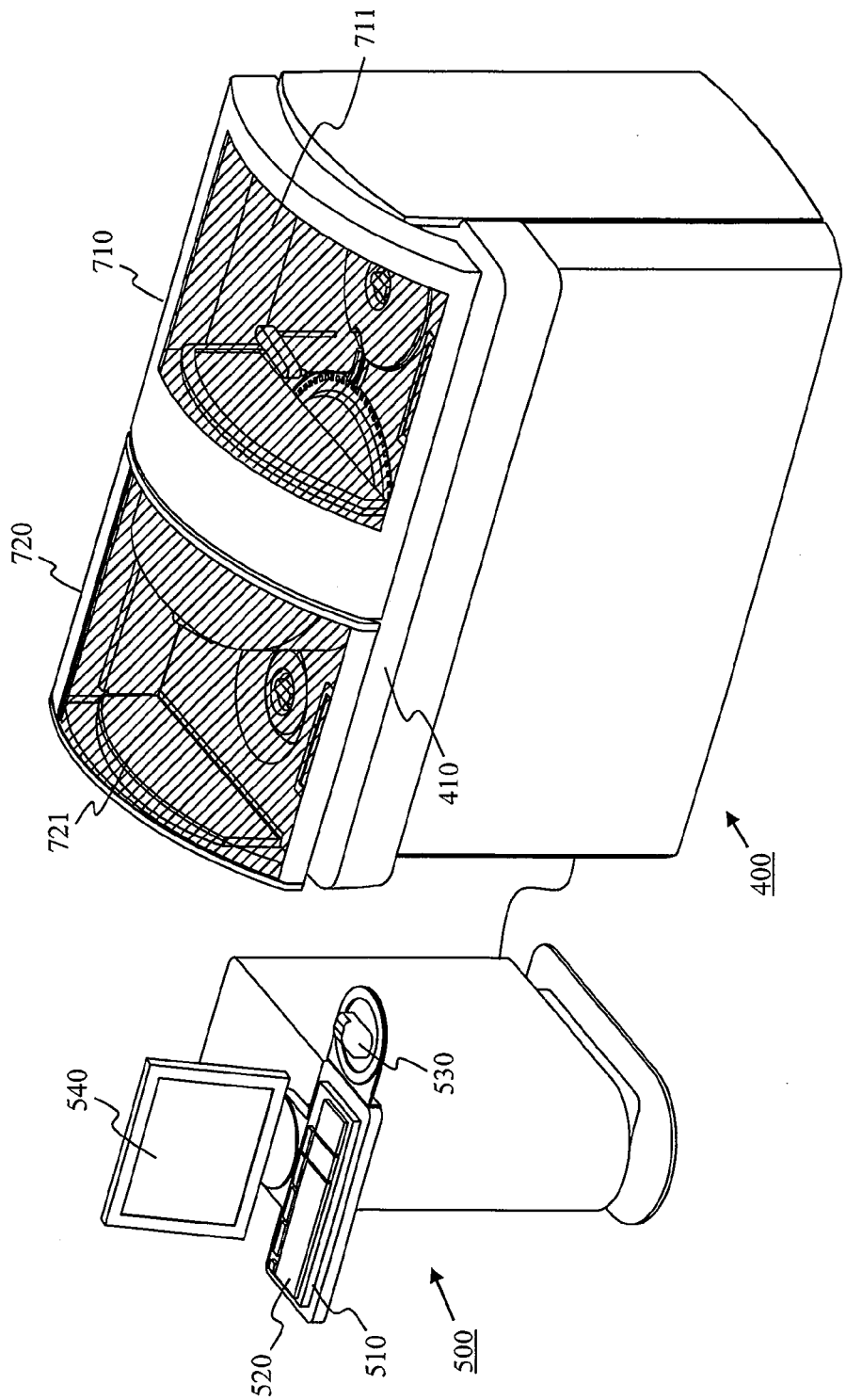
FIG. 12 schematically shows another embodiment of the automatic analysis device according to the present invention.

FIG. 12 schematically shows Embodiment 2 of the automatic analysis device according to the present invention. Embodiment 2 is different from Embodiment 1 only in the protective cover that is provided at the area above the main-body casing of the automatic analysis device, and other configuration is the same as that of Embodiment 1.

Embodiment 1 includes the three-divided structured protective cover that is made up of the first protective cover at a center part and having a light-shielding function, and the second and the third protective covers provided on either side. The present embodiment includes a two-divided structured protective cover including left and right two protective covers. A first protective cover 710 disposed on the right side of the present embodiment corresponds to the integration of the first protective cover 610 and the third protective cover 630 described in Embodiment 1, and has a function to shield a scattered light measurement unit from external light. The second protective cover 720 placed on the left side of the present embodiment has a substantially same structure as that of the second protective cover 620 in Embodiment 1.

When the first protective cover 710 and the second protective cover 720 are closed, a side end part of the second protective cover 720 is overlapped on a side end part of the first protective cover 710. This means that the second protective cover 720 can be opened/closed independently from the first protective cover 710. Meanwhile, the first protective cover 710 can be opened after the second protective cover is opened or cannot be opened unless it is opened concurrently with the second protective cover.

Therefore, when there is a need to access a sample disk during the operation of the automatic analysis device, an operator is allowed to open the second protective cover 720 on the left side and freely access the sample disk. At this time, since the first protective cover 710 on the right side is closed, the light-shielding state of a scattered light measurement unit from external light can be maintained, and so scattered light measurement is not influenced. The left and right protective covers 710, 720 are provided with see-through parts 711, 721, respectively. This allows an operator to visually check the states of various disks and the motion of dispensing mechanisms through the see-through parts of the protective covers while keeping the protective covers closed, thus knowing the operation state of the device easily and so they can continue the analysis with security. The see-through parts 711, 721 do not have to be necessarily made of a high light-transmissive material that is clear and colorless, and may be colored as long as it enables seeing therethrough. The second protective cover 720 on the left side as a whole may be made of a light-transmissive material.

During the operation of the automatic analysis device, the sample disk has to be often accessed to, after finishing an analysis of a sample, replace the sample with a new sample or to dispose a sample whose analysis result has to be known quickly by interrupting the analysis of another sample that is already set at the sample disk, for example. On the other hand, once a reagent disk is filled with a reagent before starting of the operation of the automatic analysis device, there is no need to add and refill a reagent frequently. Therefore in the case of usage where it is known that the number of samples to be analyzed is a certain number or less and that there is no need to refill a reagent during the operation time in a day, the operability of the automatic analysis device will not deteriorate even with the present embodiment having a two-divided structured protective cover. The present embodiment also can prevent external light from leaking into the scattered light measurement unit, and so enables high-precision scattered light measurement.

The left and right protective covers 710, 720 have rotary axes at their rear end parts, which are configured coaxially. Therefore, the two protective covers 710, 720 can be opened/closed concurrently and smoothly. In this way, when the two protective covers are open at the same time, fully-access is enabled to the top face 410 of the main-body casing, whereby an operator can freely perform the maintenance operations such as cleaning of the top face of the main-body casing, cleaning of the nozzles of the sample dispensing mechanism and the reagent dispensing mechanism, washing and replacing of reaction containers without constraints.

Similarly to Embodiment 1, the protective cover 710 on the right side of the present embodiment also may be equipped with a lock mechanism so as to prevent the operator from opening the protective cover 710 on the right side carelessly during the operation, the cover having an external-light shielding function for the scattered light measurement unit. A sensor may be provided to detect an opening/closing state of the protective cover 710 on the right side having an external-light shielding function, and if the protective cover on the right side is not closed, an alarm may be displayed at the manipulation/control unit, or the operation of the device may be disabled.

Embodiment 3

FIG. 13 schematically shows Embodiment 3 of the automatic analysis device according to the present invention. Embodiment 3 is different from Embodiment 1 and Embodiment 2 only in the protective cover that is provided at an area above the main-body casing of the automatic analysis device, and other configuration is the same as that of Embodiment 1 and Embodiment 2.

The protective cover of the present embodiment includes one protective cover 810 that basically corresponds to the integration of the two-divided type left and right protective covers described in Embodiment 2. Herein, although the left-side cover of Embodiment 2 is a transparent cover, the protective cover of the present embodiment has a part corresponding to it that is made of an opaque member having a light-shielding property, and instead, includes a small opening/closing door 820 made of a transparent material, which functions as a see-through part as well, at an area corresponding to the area above the sample disk 110. Since the roof part 617 of the protruding part 616 that comes with the center first protective cover 610 of Embodiment 1 and is covered with the second protective cover 620 can be eliminated because it is substituted with the protective cover 810 of the present embodiment. However, it is better to provide the side wall 618 of the protruding part 616 and the light-shielding wall 613 described in FIG. 10 for improved light-shielding performance. According to the present embodiment, since the opaque part having light-shielding property of the protective cover 810 covers the area above the sample dispensing mechanism, external light entering the scattered light measurement unit can be made less, which contributes to improve the measurement accuracy.

Since the protective cover 810 of the present embodiment has the small transparent opening/closing door 820 for accessing to the sample disk 110, if there arises a need to access the sample disk 110 during the operation of the automatic analysis device, the operator is allowed to open the opening/closing door 820 and access the sample disk 110 freely without influencing on the measurement. The operator is also allowed to check the progress of the analysis of a sample mounted on the sample disk through the transparent opening/closing door 820 while keeping the protective cover 810 and the opening/closing door 820 closed. Then, a see-through part 830 is provided at a position above the reagent disk and the reagent dispensing mechanism. This allows an operator to visually check the states of the reagent disk and the motion of the reagent dispensing mechanism through the see-through part 830 while keeping the protective cover 810 closed, thus knowing the operation state of the device easily and so they can continue the analysis with security. The transparent opening/closing door 820 and the see-through part 830 do not have to be necessarily made of a high light-transmissive material that is clear and colorless, and may be colored as long as it enables seeing therethrough.

When the protective cover 810 is open, fully-access is enabled to the top face 410 of the main-body casing, whereby an operator can freely perform the maintenance operations such as cleaning of the top face of the main-body casing, cleaning of the nozzles of the sample dispensing mechanism and the reagent dispensing mechanism, washing and replacing of reaction containers.

The protective cover 810 of the present embodiment also may be equipped with a lock mechanism as described in Embodiment 1 so as to prevent the operator from opening the cover carelessly during operation, the protective cover 810 having an external-light shielding function for the scattered light measurement unit. A sensor may be provided to detect an opening/closing state of the protective cover 810 having an external-light shielding function, and if the protective cover 810 is not closed, an alarm may be displayed at the manipulation/control unit, or the operation of the device may be disabled.

The present invention is not limited to the above-described embodiments, and may include various modification examples. For instance, the entire detailed configuration of the embodiments described above for explanatory convenience is not always necessary for the present invention. A part of one embodiment may be replaced with the configuration of another embodiment, or the configuration of one embodiment may be added to the configuration of another embodiment. The configuration of each embodiment may additionally include another configuration, or a part of the configuration may be deleted or replaced.

REFERENCE SIGNS LIST 110 sample disk
111 sample cup
120 reagent disk
121 reagent bottle
150 reaction disk
151 reaction cell
155 stirrer unit
156 washing unit
157 constant-temperature fluid
210 sample dispensing mechanism
211 support column
212 arm
213 nozzle
220 reagent dispensing mechanism
310 scattered light measurement unit
311 light source
313 scattered light
314 scattered light photoreceptor
400 analysis device main body
410 casing top face
500 manipulation/control unit
510 PC
610 first protective cover
611 tongue part
612 pin
613 light-shielding wall
614 cutout
615 main-body part
616 protruding part
617 roof part
618 side wall
619 opening
620 second protective cover
621 see-through part
630 third protective cover
631 see-through part
710 first protective cover
711 see-through part
720 second protective cover
721 see-through part
810 protective cover
820 transparent opening/closing door
830 see-through part

The invention claimed is:

1. An automatic analysis device comprising:
a sample disk, a reagent disk, a reaction disk and a plurality of dispensing mechanisms that are disposed on a top face of a main-body casing, the sample disk holding a plurality samples, the reagent disk holding a plurality of types of reagent, the reaction disk holding a plurality of reaction cells, the plurality of dispensing mechanisms each including an arm that rotates and a nozzle fixed to the arm and dispensing the samples and the reagent to the reaction cells held at the reaction disk,
a scattered light measurement unit disposed inside the main-body casing, and including a light source that applies light to the reaction cells and a photoreceptor that receives scattered light generated from a reaction liquid in the reaction cells irradiated with the light; and
a protective cover that is disposed to cover the top face of the main-body casing, and includes a light-shielding part to block external light and a see-through part enabling seeing therethrough, wherein:
the protective cover includes a first protective cover including the light-shielding part and a second protective cover including the see-through part,
the light-shielding part covers at least an area of the reaction disk corresponding to an area above the scattered light measurement unit, the first protective cover has an underlapping portion having a position with respect to an overlapping part of the second protective cover such that the overlapping part of the second protective cover overlaps the underlapping portion of the first protective cover when the first protective cover and the second protective cover are closed, based on the position of the underlapping portion with respect to the overlapping part, the second protective cover is openable independently of the first protective cover, and based on the position of the underlapping portion with respect to the overlapping part, the first protective cover is openable at least one of after or concurrently with opening of the second protective cover.

2. The automatic analysis device according to claim 1, wherein, when the second protective cover is opened independently and the first protective cover remains closed, the light-shielding part of the first protective cover continues to cover the area above the scattered light measurement unit.

3. The automatic analysis device according to claim 1, wherein, based at least in part on the overlapping part of the second protective cover overlapping the underlapping portion of the first protective cover, opening of the first protective cover causes opening of the second protective cover.

4. The automatic analysis device according to claim 1, wherein:

the protective cover includes the first protective cover including the light-shielding part, the second protective cover and a third protective cover are located on either side of the first protective cover, the second protective cover includes the see-through part and the third protective cover includes another see-through part, and the second protective cover and the third protective cover are positioned to be opened independently of each other and the first protective cover.

5. The automatic analysis device according to claim 4, wherein:

when the first protective cover and the second protective cover are closed, the overlapping part of the second protective cover overlaps the underlapping portion of the first protective cover, and when the first protective cover and the third protective cover are closed, an overlapping part of the third protective cover overlaps another underlapping portion of the first protective cover.

6. The automatic analysis device according to claim 4, wherein the first protective cover is positioned to open at least one of after or concurrently with opening of the second protective cover and the third protective cover.

7. The automatic analysis device according to claim 4, wherein, based at least in part on the overlapping part of the second protective cover overlapping the underlapping portion of the first protective cover and the overlapping part of the third protective cover overlapping the other underlapping portion of the first protective cover, opening of the first protective cover causes opening of the second protective cover and the third protective cover.

8. The automatic analysis device according to claim 1, wherein the light-shielding part has a shape that does not interfere with motion of the dispensing mechanisms.

9. The automatic analysis device according to claim 8, further comprising a light-shielding wall that has a shape along a travelling path of a nozzle of the dispensing mechanism and is disposed on the top face of the main-body casing.

10. The automatic analysis device according to claim 1, further comprising a detection unit that detects that the light-shielding part is opened.

11. The automatic analysis device according to claim 1, further comprising a lock mechanism that locks at least the light-shielding part so as to constrain opening.

* * * * *